US00PP28798P3

(12) United States Plant Patent
van den Hoogen

(10) Patent No.: US PP28,798 P3
(45) Date of Patent: Dec. 26, 2017

(54) ***VERONICA* PLANT NAMED 'ALLVGLOVE'**

(50) Latin Name: ***Veronica longifolia*×*Veronica spicata***
Varietal Denomination: Allvglove

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 70 days.

(21) Appl. No.: 14/998,862

(22) Filed: Feb. 23, 2016

(65) Prior Publication Data

US 2017/0245411 P1 Aug. 24, 2017

(51) Int. Cl.
*A01H 5/02* (2006.01)

(52) U.S. Cl.
USPC ..... Plt./251

(58) Field of Classification Search
USPC ..... Plt./251
See application file for complete search history.

(56) References Cited

PUBLICATIONS

UPOV hit on *Veronica* plant named 'Allvglove', QZ PBR 20151763, published Oct. 15, 2015.*

* cited by examiner

*Primary Examiner* — Anne Grunberg
(74) *Attorney, Agent, or Firm* — C. A. Whealy

(57) ABSTRACT

A new and distinct cultivar of *Veronica* plant named 'Allvglove', characterized by its upright plant habit; freely flowering habit; dense inflorescences with numerous purple violet-colored flowers; early flowering habit and long flowering period; and suitability as a garden or container plant.

2 Drawing Sheets

Botanical designation: *Veronica longifolia*×*Veronica spicata*.

Cultivar denomination: 'ALLVGLOVE'.

BACKGROUND OF THE INVENTION

The present invention relates to a new and distinct cultivar of *Veronica* plant, botanically known as *Veronica longifolia*× *Veronica spicata* and hereinafter referred to by the name 'Allvglove'.

The new *Veronica* plant is a product of a planned breeding program conducted by the Inventor in Rijswijk, The Netherlands. The objective of the breeding program is to create new compact and attractive *Veronica* plants with good garden performance.

The new *Veronica* plant originated from a cross-pollination of *Veronica longifolia* 'Alllove', disclosed in U.S. Plant Pat. No. 21,478, as the female, or seed, parent with *Veronica longifolia* 'Alllord', disclosed in U.S. Plant Pat. No. 23,294, as the male, or pollen, parent. The new *Veronica* plant was discovered and selected by the Inventor as a single flowering plant from within the progeny of the stated cross-pollination in a controlled environment in Rijswijk, The Netherlands on Jun. 12, 2015.

Asexual reproduction of the new *Veronica* plant by vegetative cuttings in a controlled environment in Rijswijk, The Netherlands, since July, 2015 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allvglove'. These characteristics in combination distinguish 'Allvglove' as a new and distinct *Veronica* plant:

1. Upright plant habit.
2. Freely flowering habit.
3. Dense inflorescences with numerous purple violet-colored flowers.
4. Long flowering period.
5. Suitable as a garden or container plant.

Plants of the new *Veronica* differ primarily from plants of the female parent, 'Alllove', in the following characteristics:

1. Plants of the new *Veronica* and 'Alllove' differ in flower color as plants of 'Alllove' have intense red purple-colored flowers.
2. Flowers of plants of the new *Veronica* are more slender than flowers of 'Alllove'.

Plants of the new *Veronica* differ primarily from plants of the male parent, 'Alllord', in flower color as plants of 'Alllord' have blue-colored flowers.

Plants of the new *Veronica* can be compared to plants of *Veronica longifolia* 'Allsurprise', not patented. In side-by-side comparisons conducted in Rijswijk, The Netherlands, plants of the new *Veronica* differ primarily from plants of 'Allsurprise' in the following characteristics:

1. Inflorescences of plants of the new *Veronica* are symmetrical whereas inflorescences of 'Allsurprise' are deformed.

2. Plants of the new *Veronica* and 'Allsurprise' differ in flower color as plants of 'Allsurprise' have dark blue-colored flowers.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Allvglove'.

The photograph at the top of the second sheet is a close-up view of typical inflorescences of 'Allvglove'.

The photograph at the bottom of the second sheet is a close-up view of the upper surface of a typical leaf of 'Allvglove'.

DETAILED BOTANICAL DESCRIPTION

Plants used for the aforementioned photographs and following description were grown during the summer in ground beds in an outdoor nursery in Rijswijk, The Netherlands and under cultural practices typical of commercial *Veronica* production. During the production of the plants, day temperatures ranged from 15° C. to 30° C. and night temperatures ranged from 6° C. to 18° C. Plants were four months old when the photographs and the description were taken. In the following description, color references are made to The Royal Horticultural Society Colour Chart, 2007 Edition, except where general terms of ordinary dictionary significance are used.

Botanical classification: *Veronica longifolia*×*Veronica spicata* 'Allvglove'.

Parentage:

*Female, or seed, parent.*—*Veronica longifolia* 'Alllove', disclosed in U.S. Plant Pat. No. 21,478.

*Male, or pollen, parent.*—*Veronica longifolia* 'Alllord', disclosed in U.S. Plant Pat. No. 23,294.

Propagation:

*Type cutting.*—Vegetative cuttings.

*Time to initiate roots, summer.*—About one to two weeks at temperatures ranging from 12° C. to 30° C.

*Time to produce a rooted young plant, summer.*—About 28 to 32 days at temperatures ranging from 12° C. to 30° C.

*Root description.*—Fine, fleshy; typically white in color, actual color of the roots is dependent on substrate composition, water quality, fertilizer type and formulation, substrate temperature and physiological age of roots.

*Rooting habit.*—Freely branching; dense.

Plant description:

*Plant type.*—Herbaceous perennial.

*Plant and growth habit.*—Broadly upright inverted triangle; freely basal branching habit with about five main stems developing per plant; moderately vigorous growth habit.

*Plant height.*—About 43 cm.

*Plant width.*—About 29.9 cm.

*Lateral branch description.*—Length: About 21.5 cm. Diameter: About 4 mm. Internode length: About 4.1 cm. Strength: Strong. Aspect: Main stems, mostly upright to outwardly leaning. Texture and luster: Densely pubescent; matte. Color: Close to between 143B and 144A.

Leaf description:

*Arrangement.*—Opposite, simple.

*Length.*—About 8 cm.

*Width.*—About 3.7 cm.

*Shape.*—Ovate to narrowly ovate; slightly carinate.

*Apex.*—Bluntly acute.

*Base.*—Truncate.

*Margin.*—Finely serrate.

*Texture and luster, upper surface.*—Moderately to densely pubescent; slightly glossy.

*Texture and luster, lower surface.*—Moderately to densely pubescent; very slightly glossy.

*Venation pattern.*—Pinnate.

*Color.*—Developing leaves, upper surface: Close to 143A. Developing leaves, lower surface: Close to 144A. Fully expanded leaves, upper surface: Close to N137A to N137B; venation, close to 147C to 147D. Fully expanded leaves, lower surface: Close to 146A; venation, close to 144A.

*Petioles.*—Length: About 1 cm. Diameter: About 2 mm to 4 mm. Texture, upper and lower surfaces: Smooth. Color, upper surface: Close to 137C. Color, lower surface: Close to 144A to 144B.

Flower description:

*Flower arrangement and shape.*—Single campanulate flowers arranged on dense terminal and axillary racemes; flowers face mostly outwardly.

*Flowering habit.*—Freely flowering habit with about 300 flowers developing per inflorescence and about 1,400 flowers developing per plant during the flowering season.

*Fragrance.*—Faint; somewhat moldy.

*Natural flowering season.*—Long flowering period; plants flower continuously from mid-June to late September in The Netherlands.

*Flower longevity as a cut flower.*—About ten days; flowers not persistent.

*Flower longevity on the plant.*—About 30 days; flowers not persistent.

*Flower buds.*—Length: About 5 mm. Diameter: About 2 mm. Shape: Ovate. Color: Close to N78B.

*Inflorescence height.*—About 12.7 cm.

*Inflorescence diameter.*—About 2.6 cm.

*Flower diameter.*—About 7 mm.

*Flower height.*—About 1 cm.

*Petals.*—Quantity and arrangement: Five in a single whorl; petals fused about 42.5% of the length from the base. Length: About 7 mm. Width: About 3 mm to 4 mm. Shape: Obovate. Apex: Obtuse. Margin: Entire. Texture and luster, upper and lower surfaces: Smooth, glabrous; matte. Color: When opening, upper surface: Close to N80A to N80B. When opening, lower surface: Close to N80A. Fully opened, upper surface: Close to N81A to N81B; color becoming closer to N82A with development. Fully opened, lower surface: Close to N81B.

*Sepals.*—Quantity and arrangement: Four in a single whorl; sepals fused about 25% of the length from the base. Length: About 3 mm to 4 mm. Width: About 1.5 mm. Shape: Narrowly ovate. Apex: Acute. Margin: Entire. Texture and luster, upper surface: Glabrous; matte. Texture and luster, lower surface:

Densely pubescent; matte. Color: When opening, upper surface: Close to 138D. When opening, lower surface: Close to 138C. Fully opened, upper and lower surfaces: Close to 138C.

*Peduncles*.—Length: About 12.5 cm. Diameter: About 3.5 mm. Aspect: Mostly upright. Strength: Strong. Texture: Smooth, glabrous. Color: Close to 144A.

*Pedicels*.—Length: About 1 mm. Diameter: About 0.75 mm. Aspect: About 45° from peduncle axis. Strength: Strong. Texture: Smooth, glabrous. Color: Close to 177A.

*Reproductive organs*.—Stamens: Quantity per flower: Two. Filament length: About 8 mm. Filament color: Close to N81B; towards the base, lighter than N81B. Anther shape: Double reniform, narrow. Anther length: About 3 mm. Anther color: Close to 72B. Pollen amount: Moderate. Pollen color: Close to 4D. Pistils: Quantity per flower: One. Pistil length: About 7 mm. Stigma shape: Clavate. Stigma color: Close to N81A. Style length: About 6.5 mm. Style color: Close to N81A. Ovary color: Close to 144C.

*Seeds and fruits*.—Seed and fruit development has not been observed on plants of the new *Veronica*.

Disease & pest resistance: Plants of the new *Veronica* have not been noted to be resistant to pathogens and pests common to *Veronica* plants.

Garden performance: Plants of the new *Veronica* have exhibited good garden performance and to be tolerant to rain, wind, high temperatures about 35° C. and to be hardy to USDA Hardiness Zone 4.

It is claimed:

1. A new and distinct *Veronica* plant named 'Allvglove' as illustrated and described.

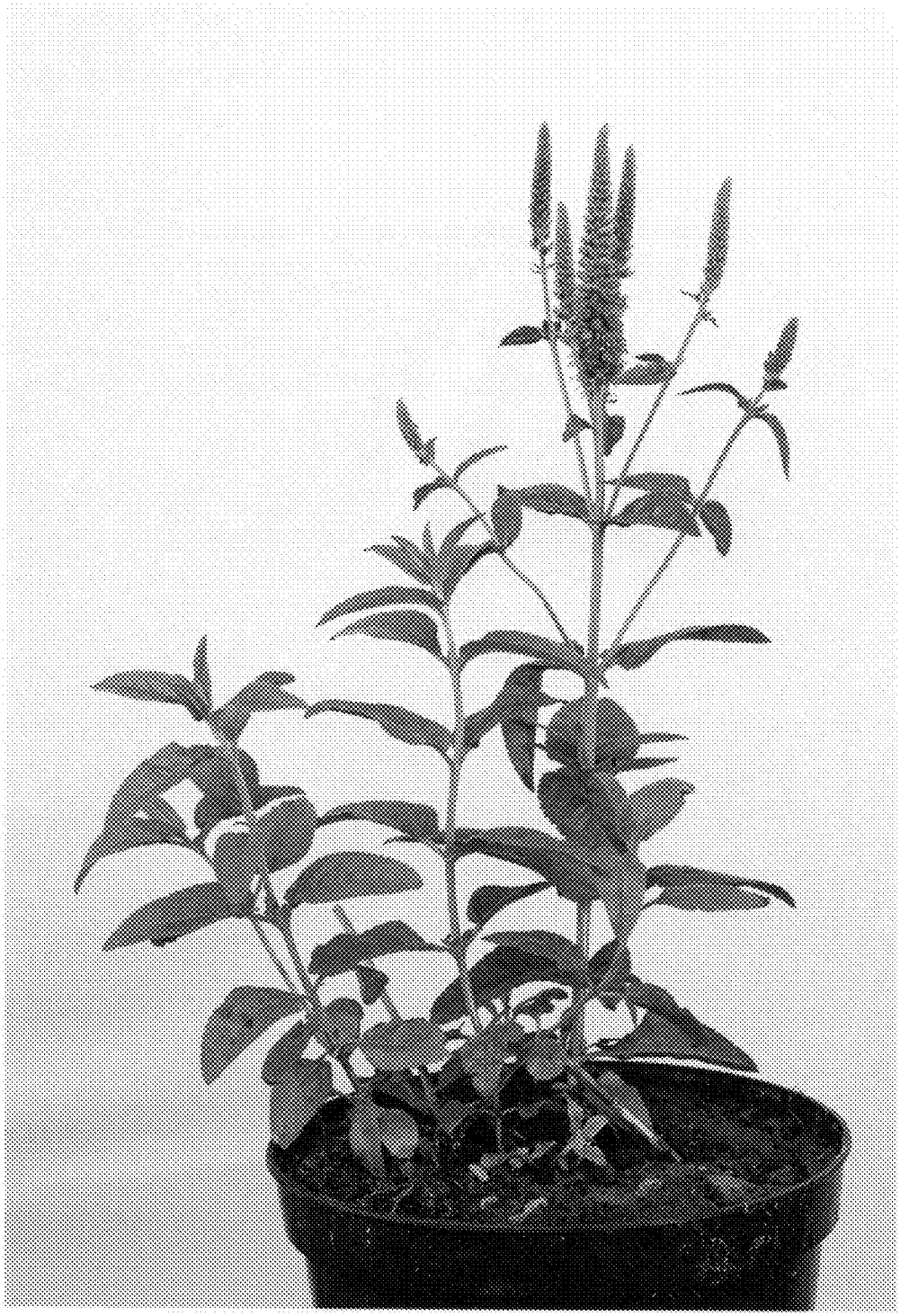

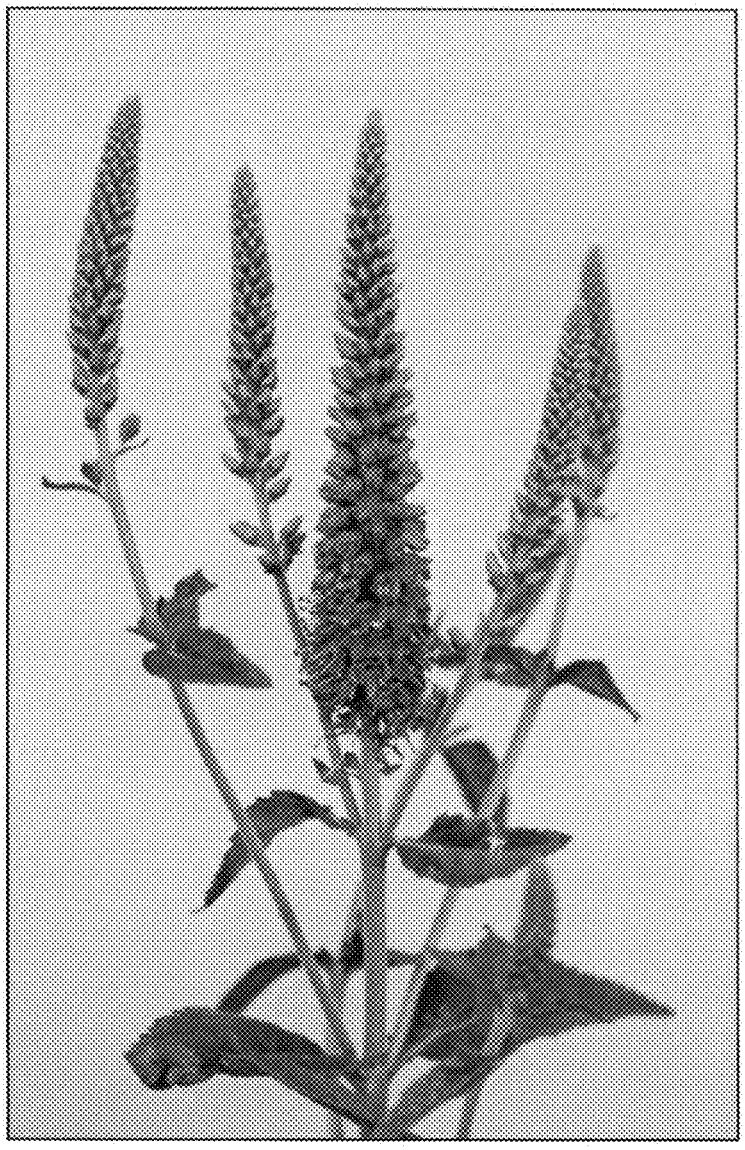
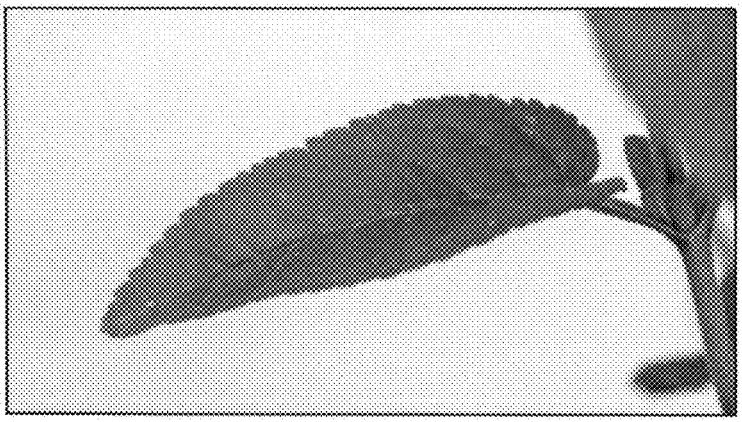

* * * * *